United States Patent [19]

Nobles, Jr.

[11] 4,007,806
[45] Feb. 15, 1977

[54] HEATED STETHOSCOPE

[76] Inventor: Eugene R. Nobles, Jr., 4184 Gwynne Road, Memphis, Tenn. 38117

[22] Filed: Apr. 7, 1976

[21] Appl. No.: 674,652

[52] U.S. Cl. .............................. 181/131; 219/201; 181/141
[51] Int. Cl.² .......................................... A61B 7/02
[58] Field of Search .................. 181/131, 137, 141; 179/1 ST; 219/201

[56] References Cited

UNITED STATES PATENTS

| 1,321,266 | 11/1919 | Wilkinson | 181/131 |
|---|---|---|---|
| 2,775,678 | 12/1956 | Flubacker | 219/201 |
| 3,213,960 | 10/1965 | Wagner | 181/126 |
| 3,366,198 | 1/1968 | Littmann | 181/137 |

Primary Examiner—Stephen J. Tomsky
Attorney, Agent, or Firm—John R. Walker, III

[57] ABSTRACT

A diaphragm type stethoscope for conveying sounds from within a patient's body to the ears of a medical examiner. A heating element is mounted within the hollow head of the stethoscope substantially adjacent the diaphragm member thereof for selectively heating the diaphragm member. A source of electrical power is preferably fixedly attached to the head of the stethoscope in electrical communication with the heating element to selectively activate the heating element.

12 Claims, 6 Drawing Figures

HEATED STETHOSCOPE

BACKGROUND OF THE INVENTION

1. Field of the Invention

This invention relates to diaphragm type stethoscopes.

2. Description of the Prior Art

Heretofore, various types of stethoscopes (e.g., the bell type, the diaphragm type, and the electronic type) have been developed for use to convey sounds from within a patient's body to a medical examiner during the medical examination of the patient. The diaphragm type stethoscope is the type most commonly used in the examination of adult patients. In using a diaphragm type stethoscope, the diaphragm member thereof is pressed against the bare skin of the patient's body to pick up sounds from within the patient's body. A major problem with the prior diaphragm type stethoscopes results from the temperature of the diaphragm member thereof being normally lower than the temperature of the patient's skin when the diaphragm member is pressed thereagainst. Such a difference in temperature creates a very uncomfortable sensation for the patient, sometimes resulting in hysterics when the patient is a young child or the like. Wagner (U.S. Pat. No. 3,213,960) discloses one method of somewhat alleviating this problem. More specifically, Wagner discloses a stethoscope head cover for insulating a stethoscope head from changes in temperature. Wagner does not completely solve the above problem. That is, merely insulating the stethoscope head from changes in temperature will not prevent discomfort to the patient caused by the difference in temperature between the stethoscope head and the patient's skin unless the temperature of the stethoscope head has been previously heated to substantially correspond to the temperature of the patient's body. Prior to the present invention, many medical examiners warmed stethoscope heads by placing the head thereof in their pockets, underneath their arms, or the like. These methods are very ineffective and do not produce uniform results.

SUMMARY OF THE INVENTION

The present invention is directed towards overcoming the problems and disadvantages of prior diaphragm type stethoscopes. The concept of the present invention is to provide a diaphragm type stethoscope with a heating means for selectively heating the diaphragm member of the stethoscope.

The stethoscope of the present invention includes: head means for being selectively pressed against a patient's body, the head means including a body member having a hollow interior and having an opened end communicating with the hollow interior, the head means including a diaphragm member extending across the opened end of the body member for selectively contacting the patient's body to pick up sounds from within the patient's body; transfer means attached to the head means for transferring any sound picked up by the diaphragm member of the head means to the medical examiner; heating means mounted within the hollow interior of the body member of the head means substantially adjacent the diaphragm member thereof for heating the diaphragm member; and a source of electrical power communicatively attached to the heating means for causing the heating means to heat the diaphragm member of the head means.

BRIEF DESCRIPTION OF THE DRAWINGS

FIG. 1 is a side elevational view of a portion of the heated stethoscope of the present invention.

FIG. 2 is a sectional view of a portion of the heated stethoscope of the present invention as taken on line II—II of FIG. 1.

FIG. 3 is a sectional view of a portion of the heated stethoscope of the present invention as taken on line III—III of FIG. 2 with some parts broken away for clarity.

FIG. 4 is a schematic view of the electrical circuit system of the heated stethoscope of the present invention.

FIG. 5 is a front view of the heated stethoscope of the present invention.

FIG. 6 is a sectional view of a portion of the heated stethoscope of the present invention as taken on line VI—VI of FIG. 1.

DESCRIPTION OF THE PREFERRED EMBODIMENT

Figures 1, 2, 3, 4, 5, 6:
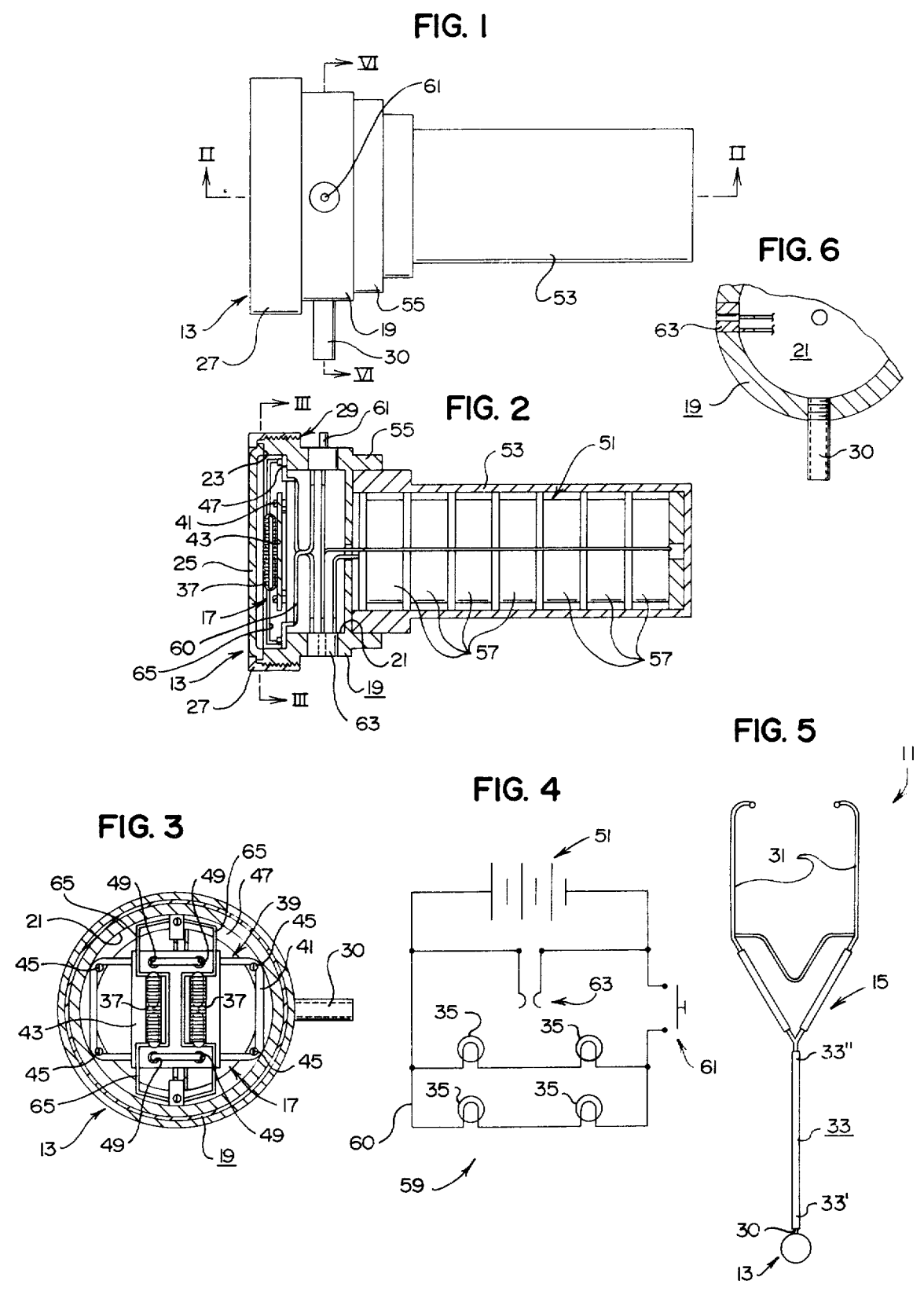

The stethoscope 11 (see FIG. 5) of the present invention is for use in the medical examination of a patient by a medical examiner such as a physician or the like to convey sounds from within the patient's body to the medical examiner. The stethoscope 11 includes, in general, head means 13 for being selectively pressed against the patient's body, transfer means 15 for transferring any sound picked up by the head means 13 to the medical examiner, heating means 17 for selectively heating the portion of the head means 13 that is pressed against the patient's body, and a source of electrical power for selectively activating the heating means 17.

The head means 13 preferably includes a body member 19 having a hollow interior 21 and having an opened end 23 communicating with the hollow interior 21 (see FIG. 2). The head means 13 also includes a diaphragm member 25 positioned over the opened end 23 of the head means 13 for selectively contacting the patient's body to pick up sounds from within the patient's body. The head means 13 preferably includes a rim member 27 removably attached to the body member 19 by way of screw threads 29 or the like for removably attaching the diaphragm member 25 to the body member 19 with the diaphragm member 25 positioned over the opened end 23 of body member 19. Additionally, the head means 13 may include a hollow stub member 30 attached to and extending outwardly from the body member 19 thereof (see FIGS. 3 & 6) for reasons which will hereinafter become apparent. It should be noted that the head means 13 as thus constructed is substantially similar to the head means of a typical stethoscope and may be constructed of the same material and in substantially the same manner as the head means of a typical stethoscope.

The transfer means 15 preferably includes a binaural ear attachment member 31 for selective placement in operative engagement with the ears of the medical examiner (see FIG. 5). The transfer means 15 also preferably includes a flexible tube member 33 having a first end 33' for being removably attached to the head means 13 in operative communication with the hollow interior 21 of the body member 19 thereof by way of the hollow stub member 30 and having a second end 33" attached to the binaural ear attachment member 31 for allowing sound to pass from within the hollow interior 21 of the body member 19 of the head means 13 through the flexible tube member 33 and to the binaural ear attachment member 31. It should be noted that the first end 33' of the tube member 33 is preferably adapted to slip over the outward end of the hollow stub member 30 (see FIG. 5) in a manner similar to a typical stethoscope. It should be noted that the binaural ear attachment 31 and the flexible tube member 33 may be of a one piece construction. In any event, the binaural ear attachment member 31 and the flexible tube member 33 of the transfer means 15 are substantially identical to a transfer means of a typical stethoscope and may be constructed of the same material and in substantially the same manner as the transfer means of a typical stethoscope.

The heating means 17 is mounted within the hollow interior 21 of the body member 19 of the head means 13 substantially adjacent the diaphragm member 25 thereof (see FIG. 2) for selectively heating the diaphragm member 25. The heating means 17 preferably includes at least one light bulb 35 mounted within the hollow interior 21 of the body member 19 substantially adjacent the diaphragm member 25. Preferably, the heating means 17 includes a plurality of light bulbs 35 for being positioned substantially adjacent a substantial area of the diaphragm member 25 for quickly and uniformly heating the diaphragm member 25. More specifically, the heating means 17 preferably includes four light bulbs 35 (see FIG. 4). Additionally, the heating means 17 preferably includes a coil 37 of heat conducting and transferring wire wrapped around each of the light bulbs 35 (see FIGS. 2 and 3). The coils 37 of heat conducting and transferring wire allows heat to be extracted from the light bulbs 35 when the light bulbs 35 are activated and allows the heat so extracted to be transferred to the diaphragm member 25. The coils 37 may be constructed of any wire well known to those skilled in the art that will conduct and transfer heat, and should be insulated. For example, the coils 37 may be constructed of a copper wire with the turns thereof being insulated from one another by suitable means, such as a coating, e.g., a laquer or enamel. The heating means 17 may be replaced as a unit upon any of the light bulbs 35 burning out.

The stethoscope 11 may include mounting means 39 for mounting the heating means 17 within the hollow interior 21 of the body member 19 of the head means 13 substantially adjacent the diaphragm member 25 thereof (see FIGS. 2 and 3). The mounting means 39 preferably includes an elastic suspension member 41 fixedly attached to the body member 19 of the head means 13 within the hollow interior 21 thereof slightly subjacent the opened end 23 of the head means 13 and preferably includes a plate member 43 mounted on the elastic suspension member 41. The elastic suspension member 41 is preferably an endless member such as a typical rubber band or the like. The elastic suspension member 41 may be fixedly attached to the body member 19 by means of a plurality of screws 45. More specifically, the screws 45 may be attached to an interior rim 47 or the like within the interior 21 of the body member 19 with a portion of each screw 45 extending from the ridge 47 so that the elastic suspension member 41 can be stretched around the screws 45. Each screw 45 is preferably provided with a head or the like so that once the elastic suspension member 41 has been stretched thereabout, the heads of the screws 45 will substantially prevent the elastic suspension member 41 from slipping off the screws 45. The plate member 43 may be mounted to the elastic suspension member 41 in any manner apparent to those skilled in the art. For example, the plate member 43 may be provided with a plurality of apertures 49 through which the elastic suspension member 41 may be threaded. The heating means 17 is supported on the plate member 43.

The source of electrical power for selectively causing the heating means 17 to heat the diaphragm member 25 may include battery means 51 (see FIGS. 2 and 4). The battery means 51 is preferably attached to the head means 13 for movement therewith. More specifically, the battery means 51 is preferably mounted within a hollow housing member 53 which is in turn attached to the head means 13. Preferably, the housing member 53 is removably attached to the head means 13 for allowing replacement of the battery means 51. More specifically, the head means 13 may be provided with a rim portion 55 of a size to frictionally receive a portion of the housing member 53 to secure the housing member 53 thereto. The battery means 51 may include a plurality of nickel cadmium battery members 57.

The stethoscope 11 may include electric circuit means 59 consisting of suitable electrical wiring 60 for connecting the battery means 51 to the light bulbs 35 of the heating means 17 (see FIG. 4). The electric circuit means 59 may include switch means 61 for allowing the light bulbs 35 to be selectively activated or deactivated. The switch means 61 is preferably spring loaded so that it will open when it is released to prevent the light bulbs 35 from inadvertently being left activated. The electric circuit means 59 may include jack means 63 for allowing a typical battery charger device to be connected to the battery means 51 to selectively recharge the battery means 51 without requiring the battery means 51 to be detached from the circuit means 59. It should be pointed out that the portion 65 of the wiring 60 connecting the light bulbs 35 to the battery means 51 is preferably flexible to allow limited movement of the heating means 17.

The stethoscope 11 of the present invention is used in substantially the same manner as a typical diaphragm type stethoscope. However, when a medical examiner is examining a patient with the stethoscope 11 of the present invention, he will heat the diaphragm member 25 of the stethoscope 11 by closing the switch means 61 thereof for a short period of time just prior to pressing the head means 13 of the stethoscope 11 against the patient's bare skin. It should be noted that by "overdriving" the light bulbs 35, the time required to heat the diaphragm member 25 of the stethoscope 11 may be substantially reduced. More specifically, by providing a battery means 51 that produces a higher electromotive force than the light bulbs 35 are rated for, the light bulbs 35 are "overdriven" to cause the heating means 17 to produce more heat than if the light bulbs 35 were not "overdriven." For example, the heating means 17 may include two groups of light bulbs 35 with each group including two 1.5 volt light bulbs 35 arranged in series to one another and with each group arranged parallel to the other group (see FIG. 4) and the battery means 51 may have an electromotive force of 8.4 volts so that the electromotive force applied to each light bulb 35 will be approximately 4.2 volts thereby causing the light bulbs 35 to be "overdriven" by approximately 2.7 volts.

As thus constructed and used, the present invention provides a diaphragm type stethoscope in which the diaphragm thereof can be quickly heated without affecting the acoustical properties of the stethoscope.

Although the invention has been described and illustrated with respect to a preferred embodiment thereof, it is not to be so limited since changes and modifications may be made therein which are within the full intended scope of the invention.

I claim:
1. A stethoscope for conveying sounds from within a patient's body to a medical examiner, said stethoscope comprising:
   a. head means for being selectively pressed against the patient's body, said head means including a body member having a hollow interior and having an opened end communicating with said hollow interior, said head means including a diaphragm member extending across said opened end of said body member for selectively contacting the patient's body to pick up sounds from within the patient's body;
   b. transfer means attached to said head means for transferring any sound picked up by said diaphragm member of said head means to the medical examiner;
   c. heating means mounted within said hollow interior of said body member of said head means substantially adjacent said diaphragm member thereof for heating said diaphragm member; and
   d. a source of electrical power communicatively attached to said heating means for causing said heating means to heat said diaphragm member of said head means.

2. The stethoscope of claim 1 in which is included mounting means for mounting said heating means within said hollow interior of said body member of said head means substantially adjacent said diaphragm member thereof; said mounting means including an elastic suspension member fixedly attached to said body member of said head means within said hollow interior thereof and including a plate member mounted on said elastic suspension member, said heating means being supported on said plate member.

3. The stethoscope of claim 2 in which said heating means includes at least one light bulb supported on said plate member of said mounting means substantially adjacent said diaphragm member of said head means and communicatively attached to said source of electrical power.

4. The stethoscope of claim 3 in which said heating means includes a coil of heat conducting and transferring wire wrapped around said at least one light bulb.

5. The stethoscope of claim 4 in which said source of electrical energy includes battery means attached to said head means for movement therewith, and in which is included electric circuit means for connecting said battery means to said at least one light bulb of said heating means.

6. The stethoscope of claim 5 in which said circuit means includes switch means for allowing said at least one light bulb to be selectively activated.

7. The stethoscope of claim 5 in which said circuit means include jack means for allowing said battery means to be selectively recharged without being detached from said circuit means.

8. A stethoscope for conveying sounds from within a patient's body to the ears of a medical examiner, said stethoscope comprising:
   a. head means for being selectively pressed against the patient's body, said head means including a body member having a hollow interior and having an opened end communicating with said hollow interior, said head means including a diaphragm member positioned over said opened end of said body member for selectively contacting the patient's body to pick up sounds from within the patient's body, said head means including a rim member removably attached to said body member for removably attaching said diaphragm member to said body member with said diaphragm member positioned over said opened end of said body member;
   b. transfer means for transferring any sound picked up by said diaphragm member of said head means to the ears of the medical examiner, said transfer means including a binaural ear attachment member for selective placement in operative engagement with the ears of the medical examiner and including a flexible tube member having a first end removably attached to said head means in operative communication with said hollow interior of said body member thereof and having a second end attached to said binaural ear attachment member for allowing sound to pass from within said hollow interior of said body member of said head means through said flexible tube member and to said binaural ear attachment member;
   c. mounting means provided within said hollow interior of said body member of said head means, said mounting means including an elastic suspension member fixedly attached to said body member of said head means within said hollow interior thereof so as to extend across said hollow interior of said body member slightly subjacent said opened end of said head means, said mounting means including a plate member mounted on said elastic suspension member substantially centrally of said hollow interior of said body member of said head means;
   d. heating means for selectively heating said diaphragm member of said head means, said heating means including a plurality of light bulbs supported on said plate member of said mounting means substantially adjacent said diaphragm member of said head means, said heating means including a coil of heat conducting and transferring wire wrapped around each of said plurality of light bulbs for extracting heat from any light produced by said plurality of light means and transferring any heat so extracted to said diaphragm member of said head means;
   e. battery means for activating said plurality of light bulbs of said heating means, said battery means being attached to said head means for movement therewith; and
   f. electric circuit means for connecting said battery means to said plurality of light bulbs of said heating means, said circuit means including switch means for allowing said plurality of light bulbs of said heating means to be selectively activated.

9. The stethoscope of claim 8 in which said switch means of said electric circuit means is spring loaded for causing said plurality of light bulbs to be deactivated automatically once said switch means is released.

10. The stethoscope of claim 8 in which said electric circuit means includes jack means for allowing said battery means to be recharged without being detached from said electric circuit means.

11. The stethoscope of claim 8 in which said battery means overdrives said plurality of light bulbs.

12. An improvement in a stethoscope of the type including a hollow head means having a diaphragm member for being selectively pressed against a patient's body to pick up sounds from within the patient's body and including transfer means for transferring any sound picked up by said diaphragm member to a medical examiner, the combination with said head means of heating means mounted within the hollow interior of said head means substantially adjacent said diaphragm member of said head means for selectively heating said diaphragm member.

* * * * *